US006232127B1

(12) United States Patent
Lane et al.

(10) Patent No.: US 6,232,127 B1
(45) Date of Patent: May 15, 2001

(54) PLATELET FUNCTION EVALUATION TECHNIQUE FOR CITRATED WHOLE BLOOD

(75) Inventors: Carole G. Lane, Englewood; Adrian C. Wilson, Denver; Robert F. Baugh, Parker, all of CO (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/330,545

(22) Filed: Jun. 11, 1999

Related U.S. Application Data (62) Division of application No. 08/846,318, filed on Apr. 30, 1997, now Pat. No. 5,951,951.

(51) Int. Cl.[7] .................................................. G01N 33/86
(52) U.S. Cl. .................................. 436/69; 436/8; 436/17; 436/18; 422/73; 435/13
(58) Field of Search .................................. 436/8, 17, 18, 436/63, 69, 174; 422/73; 435/13

(56) References Cited

U.S. PATENT DOCUMENTS

| | | | |
|---|---|---|---|
| 3,985,618 | 10/1976 | Innerfield | 195/103.5 R |
| 4,443,408 | 4/1984 | Mintz | 422/73 |
| 4,551,308 | 11/1985 | Mintz | 422/58 |
| 4,599,219 | 7/1986 | Cooper et al. | 422/61 |
| 4,671,939 | 6/1987 | Mintz | 422/58 |
| 4,720,787 | 1/1988 | Lipscomb | 364/416 |
| 4,782,026 | 11/1988 | Baugh et al. | 436/69 |
| 4,788,139 | 11/1988 | Ryan | 435/13 |
| 4,871,677 | 10/1989 | Baugh et al. | 436/69 |
| 5,091,304 | 2/1992 | La Duca et al. | 435/13 |
| 5,174,961 | 12/1992 | Smith | 422/73 |
| 5,207,988 | 5/1993 | Lucas | 422/73 |
| 5,266,462 | 11/1993 | Hemker et al. | 435/13 |
| 5,314,826 | 5/1994 | Baugh | 436/69 |
| 5,441,892 | 8/1995 | Baugh | 436/69 |
| 5,472,852 | 12/1995 | Smirnov et al. | 435/13 |
| 5,525,477 | 6/1996 | Hassouna | 435/13 |
| 5,525,478 | 6/1996 | Matschiner | 435/13 |
| 5,563,041 | 10/1996 | Martin | 435/13 |
| 5,602,037 | 2/1997 | Ostgaard et al. | 4636/69 |
| 5,925,319 | * 7/1999 | Baugh et al. | 422/73 |
| 5,972,712 | * 10/1999 | Baugh et al. | 436/69 |
| 6,010,911 | * 1/2000 | Baugh et al. | 436/69 |

OTHER PUBLICATIONS

"Platelet Activating Factor," Demopoulos, et al., *The Journal of Biological Chemistry*, V. 254, No. 19, pp. 9355–9358. (Oct. 10, 1979).

* cited by examiner

*Primary Examiner*—Maureen M. Wallenhorst
(74) *Attorney, Agent, or Firm*—Hogan & Hartson, LLP; Steven C. Petersen (57) ABSTRACT

An improved apparatus and method for evaluating platelet functionality of a blood sample. The apparatus includes a plurality of test cells. Each of the cells includes a platelet function restoration agent, an anticoagulant agent, and a clotting reagent. At least one of the cells also includes a platelet activating agent. The clotting time is determined for each of the aliquot portions, and the relative clotting times of the aliquot portions in the cells are determinative of the platelet functionality of the sample. The method includes the steps of combining a platelet function restoration agent, an anticoagulant agent, a platelet activating agent, and the sample of blood to be tested to form a test mixture. The platelets of the sample are activated by adding a clotting reagent to the test mixture at the start of the activated clotting time test, and the activated clotting time test is terminated upon detecting a predetermined change in a property of the test mixture. The activated clotting time of the sample of blood is calculated based on the elapsed time.

14 Claims, 5 Drawing Sheets

PLATELET FUNCTION EVALUATION TECHNIQUE FOR CITRATED WHOLE BLOOD

CROSS-REFERENCE TO OTHER APPLICATIONS

This application is a divisional of U.S. patent application Ser. No. 08/846,318, filed Apr. 30, 1997, now U.S. Pat. No. 5,951,951, issued on Sep. 14, 1999.

BACKGROUND OF THE INVENTION

1. Field of the Invention

The present invention relates to measuring and detecting coagulation and coagulation-related activities in fluids, particularly human blood. More particularly, the present invention relates to an improved activated clotting time test for citrated blood samples which provides accurate and reliable detection of coagulation-related activities regardless of the amount of time which has elapsed since the sample was drawn.

2. Description of the State of the Art

Blood coagulation is a complex chemical and physical reaction which occurs when blood comes into contact with an activating agent, such as an activating surface or an activating reagent. In accordance with one simplified conceptual view, the whole blood coagulation process can be generally viewed as three activities: platelet adhesion, platelet aggregation, and formation of a fibrin clot. In vivo, platelets flow through the blood vessels in an inactivated state because the blood vessel lining, the endothelium, prevents activation of platelets. When a blood vessel is damaged, however, the endothelium loses its integrity and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced which causes conversion of fibrinogen to fibrin, which forms the major portion of the clot mass. During clotting, additional platelets are activated and trapped in the forming clot, contributing to clot formation. As clotting proceeds, polymerization and cross-linking of fibrin serves as the permanent clot. Thus, platelet activation plays a very important function in blood coagulation.

A number of different medical apparatuses and testing methods exist for measuring and determining coagulation and coagulation-related activities of blood. These apparatuses and methods provide valuable medical information to an attending physician. For example, the information assists a physician in prescribing medication, predicting post-operative bleeding and prescribing various therapies. Some of the more successful techniques of evaluating blood clotting and coagulation are the plunger techniques illustrated by U.S. Pat. No. 4,599,219 to Cooper et al., U.S. Pat. No. 4,752,449 to Jackson et al., and U.S. Pat. No. 5,174,961 to Smith, all of which are assigned to the assignee of the present invention, and all of which are incorporated herein by reference.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends by the force of gravity, resisted by a property of the fluid in the reaction chamber, such as its viscosity. When the property of the sample changes in a predetermined manner as a result of the onset or occurrence of a coagulation-related activity, the descent rate of the plunger assembly therethrough is changed. Upon a sufficient change in the descent rate, the coagulation-related activity is detected and indicated by the apparatus.

Certain discoveries have been made which contribute to a better understanding of the role of platelets in an ACT test. Such discoveries suggest that the activation of the platelets has a significant and previously unappreciated effect on ACT test results. While it has long been suspected that platelet activation contributes to total blood coagulation times, until fairly recently, there has been no technique available for confirming and quantifying the impact of platelet activation on ACT. U.S. Pat. No. 5,314,826 to Baugh describes an improved ACT test which includes a platelet activation phase to accommodate the effects of platelet activation. In the platelet activation phase an activating reagent is mixed with a sample of blood to be tested, then the mixture is gently agitated in such a manner and for a period of time sufficient to establish a predetermined and predictable contribution to the ACT from platelet activation. To evaluate platelet function, two simultaneous ACT tests (with different platelet activation phases) are performed, and the difference between the ACTs is indicative of the platelet functionality of the sample of blood. In a further improvement, described in U.S. Ser. No. 08/640,275, filed Apr. 30, 1996, the sample of blood is mixed with a chemical platelet activating agent to facilitate the participation of active platelets in the blood clotting reaction, thereby shortening the clotting time of the blood. If the platelets are inactive or not functioning normally, the activator will have minimal or no effect on the clotting time. Both U.S. Pat. Nos. 5,314,826 and 5,925,319 are assigned to the assignee of the present invention, and are incorporated by reference in their entireties herein.

Although previous apparatuses using the plunger sensing technique have proven generally satisfactory, the need for certain enhancements has been identified. Specifically, while these techniques can measure and detect coagulation and coagulation-related activities in a sample of blood, none are designed to reliably reflect the true in vivo coagulation conditions regardless of the amount of time which has lapsed since the blood sample was drawn. Most of the apparatuses currently available for monitoring platelet function are designed specifically for freshly drawn blood, or the test must be performed on a sample of citrated whole blood at a predetermined time after the blood is drawn, for reasons which will be discussed below. Citrated whole blood is whole blood collected in a medium containing a calcium chelating agent, such as sodium citrate (citrate). The whole blood is mixed with the citrate or calcium chelating agent when the sample is collected.

Calcium plays a significant role in the analysis of blood clotting. The act of drawing blood initiates clotting reactions, and unless something is done to stop the process, the clotting times have no diagnostic significance. The formation of a clot is a multi-step process and several of these steps require the presence of calcium ions. By removing the calcium ions, as is the effect when the blood is collected in citrate, the blood can be prevented from clotting. To reinitiate the clot-forming process, calcium is added back into the whole blood (recalcification). Many ACT tests, including many platelet function assays, can be performed on blood which has been collected into a medium containing a calcium chelating agent. A calcium chelating agent is a chemical which reacts with the calcium in such a fashion that the calcium can no longer function in blood coagulation. The most common chelating agent is a salt of citric acid (citrate), since it has the fewest side effects on the components of the clotting system. By collecting blood into a medium containing a calcium chelating agent such as citric acid, sample collection and the assay on the citrated sample can be separated by a time period of up to several hours.

Most hospitals and laboratories would like to be able to use citrated whole blood. The use of citrated whole blood means that the assay does not have to be run at bedside, and allows transport of the sample from the patient to a clinical laboratory for testing. Existing coagulation detection apparatuses can perform ACT tests on recalcified samples of whole blood collected initially in citrate or in some other calcium chelating agent, to thereby provide the convenience for delaying the assay from the time when the blood sample was collected. Unfortunately, for many individuals, there is a marked difference in results of an ACT test run at bedside and a recalcified ACT test on a citrated whole blood sample. In an ACT test performed on fresh drawn whole blood, the contribution of platelets is rate limiting. However, in a recalcified ACT test performed on citrated whole blood at a significant time after collection of the sample, some component of platelet participation has been activated. Consequently, the time component of coagulation required to form this activity is not reflected in the recalcified ACT test results because the activity has partially or fully developed. Thus, after approximately the first 30–60 minutes after drawing the blood sample in citrate, the coagulation component from platelet activity has concluded and, consequently, when the recalcified ACT test is performed, the amount of time for the activation is not included within the results of the ACT test. The recalcified activated clotting times of the citrated blood get shorter and shorter until activation is complete. The magnitude of this initial drop in the activated clotting time depends upon the elapsed time after drawing the sample, as well as the individual subject or patient from whom the blood was drawn. Platelets in a stored citrated sample become activated at a rate and to a degree which varies from individual to individual.

Thus, to obtain ACT test results which reliably reflect the true condition of platelets in vivo, the ACT test must be performed either at bedside approximately contemporaneously with drawing the blood sample or at a predetermined time after collection to extrapolate the patient's baseline (non-activated) clotting time. When the test cannot be performed at bedside, the time of draw must be specified on the sample tube, as well as instructions regarding the timing of the test(s). Not only does this time factor complicate the performance of ACT tests, but such tests are generally subject to variable results and inaccuracies because individual variations in collection and test procedures are introduced by the technicians processing the samples and conducting the tests.

A need therefore exists for an improved activated clotting time test which can accurately and reliably detect coagulation and coagulation-related activities in blood samples regardless of the amount of time which has elapsed since the sample was obtained. The ability to measure and evaluate platelet activation and function independent of the time interval between collection and testing is important, particularly when the blood sample must be transported to a different location for evaluation. At the present time, there is no known apparatus or method which is universally applicable to both fresh-drawn blood and citrated whole blood which has been stored for an unspecified amount of time.

SUMMARY OF THE INVENTION

Accordingly, it is a general object of the present invention to provide an improved activated clotting time test.

It is a more specific object of the present invention to provide an improved activated clotting time test which can detect coagulation and coagulation-related activities, and particularly platelet function-related activities, in a citrated blood sample regardless of the amount of time which has elapsed since the sample was obtained.

It is further an object of the present invention to provide an improved activated clotting time test which reliably reflects the true in vivo platelet function, and which can accommodate citrated whole blood which has been stored for an unspecified length of time.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, the present invention is directed to an apparatus for performing a platelet functionality test on a blood sample. The apparatus comprises a plurality of test cells. Each of the cells comprises a platelet function restoration agent, an anticoagulant agent and a clotting reagent. At least one of the cells further comprises a platelet activating agent. A clotting time is determined for each of the aliquot portions, and the relative clotting times of the aliquot portions in the cells are determinative of the platelet functionality of the sample.

The present invention is also directed to an apparatus for performing a platelet functionality test on a blood sample containing platelets. The apparatus comprises a plurality of test cells. Each of the cells comprises heparin, kaolin, and a sufficient quantity of calcium chloride to achieve optimal platelet function in the blood sample. At least one of the cells further comprises platelet activating factor. A clotting time is determined for each of the aliquot portions, and the relative clotting times of the aliquot portions in the cells are determinative of the platelet functionality of the sample.

The present invention is further directed to an apparatus for performing a platelet functionality test on blood containing platelets using a plunger sensor technique. The apparatus comprises a cartridge having first and second test cells, each test cell containing a platelet function restoration agent, an anticoagulant agent and a clotting reagent. The first test cell further comprises a platelet activating agent. A clotting time is determined for each of the test cells, and the relative clotting times of the cells are determinative of the platelet functionality of the blood.

The present invention is also directed to a method for performing an activated clotting time test on a sample of blood containing platelets. The method comprises the steps of combining a platelet function restoration agent, an anticoagulant agent, a platelet activating agent, and the sample of blood to be tested to form a test mixture. The platelets of the sample are activated by adding a clotting reagent to the test mixture at the start of the activated clotting time test, and the test is terminated upon detecting a predetermined change in a property of the test mixture. The activated clotting time of the sample of blood is calculated based on the elapsed time.

The present invention is also directed to a method for performing an activated clotting time test on a sample of blood containing platelets using a plunger sensor apparatus. The apparatus comprises at least one test cell and a plunger assembly within the test cell. The test cell includes a reaction chamber and a reagent chamber, the reaction chamber comprising a platelet function restoration agent, an anticoagulant agent, and a platelet activating agent. The reagent chamber comprises a clotting reagent. The method comprises the steps of dispensing a sample of blood into the reaction chamber to form a first test mixture, then combining the first test mixture with the clotting reagent from the reagent chamber to form a second test mixture. The plunger assembly is reciprocated in the second test mixture by alternately lifting the plunger assembly and allowing the plunger assembly to descent through the test mixture. The point in time at which a predetermined property of the second test mixture changes by a predetermined expected amount is detected by sensing the descent of the plunger assembly, the predetermined property affecting the activated clotting time test. The elapsed time is measured from the beginning of the step of combining the first test mixture with the clotting reagent to the point in time at which the property of the second test mixture changes by the predetermined expected amount, and the activated clotting time of the sample of blood is calculated based on the elapsed time.

The present invention is further directed to a method for performing an activated clotting time test on a sample of blood containing platelets using a plunger sensor apparatus. The apparatus comprises at least one test cell and a plunger assembly within the test cell. The test cell includes a reaction chamber and a reagent chamber, the reaction chamber comprising heparin, platelet activating factor, and a sufficient quantity of calcium chloride to achieve optimal platelet function in the blood sample. The reagent chamber comprises kaolin. The method comprises the steps of dispensing a sample of blood into the reaction chamber to form a first test mixture, then combining the first test mixture with the kaolin from the reagent chamber to form a second test mixture. The plunger assembly is reciprocated in the second test mixture by alternately lifting the plunger assembly and allowing the plunger assembly to descent through the test mixture. A point in time at which a predetermined property of the second test mixture changes by a predetermined expected amount is detected by sensing the descent of the plunger assembly, the predetermined property affecting the activated clotting time test. An elapsed time is measured from the beginning of the step of combining the first test mixture with the kaolin to the point in time at which the property of the second test mixture changes by the predetermined expected amount. The activated clotting time of the sample of blood is calculated based on the elapsed time.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings

DETAILED DESCRIPTION OF THE PREFERRED EMBODIMENTS

The present invention provides a solution to the problem relating to the initial drop in recalcified activated clotting times of citrated whole blood samples. This initial drop in recalcified activated clotting times is believed to result from a platelet procoagulant activity which commences after drawing the blood sample, even though the blood sample is collected in citrate or some other calcium chelating agent. To eliminate the initial drop in activated clotting times, and thus more accurately reflect the true in vivo coagulation conditions, it was discovered that the effects of the platelet procoagulant activity can be reversed by mixing the citrated whole blood with a calcium source prior to performing the activated clotting time test. The method of the present invention thus involves a pre-test recalcification step to reestablish the in vivo platelet function in the citrated blood sample prior to commencing the test. Contemporaneously with the pre-test recalcification, an anticoagulant is introduced into the blood sample to inhibit pre-test coagulation and coagulation-related reactions. In a preferred embodiment, the calcium source and anticoagulant are included as test reagents in the test cell, and dissolved in the blood sample within the cell prior to commencing the activated clotting time test, i.e., prior to introducing the clotting reagent into the test mixture.

Figure 1:
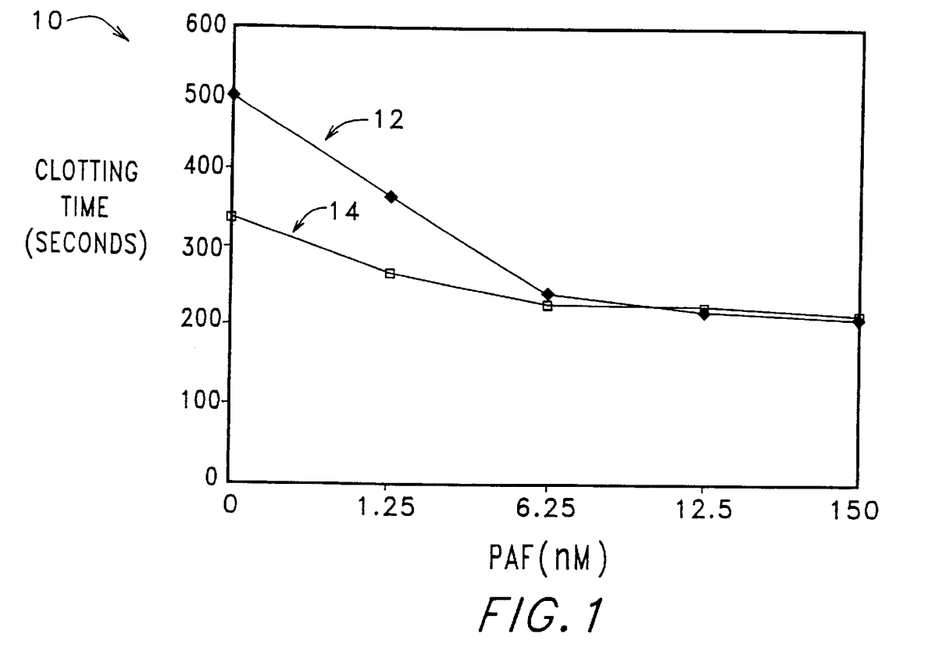
FIG. 1 is a graph of activated clotting times of whole blood vs. the concentration of platelet activating factor (PAF), showing the effects of storage in sodium citrate (anticoagulant) on clotting time. The upper curve 12 of the graph represents the behavior of a sample of fresh whole blood, tested within one minute of drawing the sample. The bottom curve 14 represents the behavior of a sample of blood from the same individual collected in a 3.8% solution of sodium citrate (referred to herein as "citrate collection medium"), specifically in a 9:1 ratio of blood to citrate collection medium, and stored for 45 minutes.

FIG. 1 presents curves 12 and 14 which compare the effects of storage time on the baseline and activated clotting times of whole blood. Curve 12 illustrates the baseline (non-activated) clotting time of fresh-drawn whole blood and the response of fresh whole blood to increasing PAF concentrations. Curve 14 illustrates the baseline clotting time of citrated whole blood and the response of citrated blood to increasing PAF concentrations. Citrated whole blood is whole blood collected in a 3.8% sodium citrate collection medium, defined as 3.8 grams of sodium citrate per 100 ml of water. A 3.8% sodium citrate collection medium is that which is frequently used to collect and preserve blood for clotting assays. Note that the baseline clotting time is less for the delayed (citrated) blood sample, due to platelet activation (i.e., platelet procoagulant activity) during the 45-minute storage period. The clotting times in the cells with PAF activation (i.e., PAF concentrations of 6.25 to 150 nM) are essentially identical for both samples. Since the platelet function evaluation is based on the difference between the activated (150 nM PAF) and non-activated (0 nM PAF) clotting times, the calculated platelet function is less for the citrated whole blood sample than for freshly drawn blood from the same individual.

Figure 2:
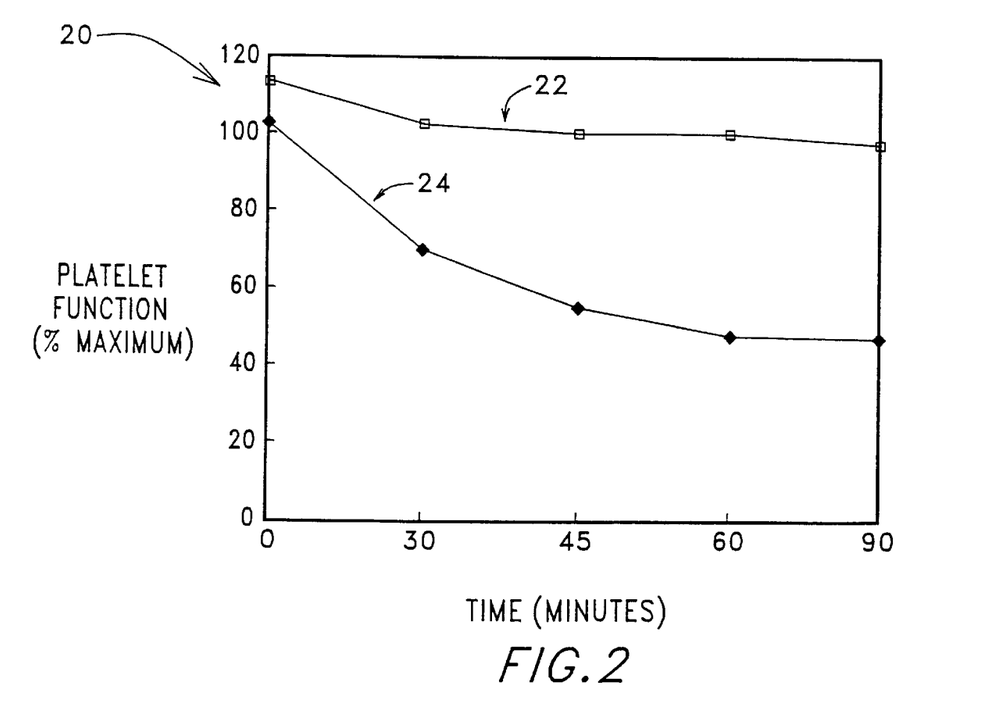
FIG. 2 is a graph of calculated platelet function of heparinized and citrated whole blood vs. the elapsed time period after which the blood sample was drawn. The upper curve 22 of the graph represents the behavior of a sample of whole blood which contains 3 units per milliliter of heparin (anticoagulant). The bottom curve 24 represents the behavior of the same blood collected in a 3.8% citrate collection medium (9:1 ratio of blood to collection medium)

FIG. 2 presents curves 22 and 24 which compare the effect of delay in testing samples of heparinized and citrated whole blood. Curve 22 illustrates the loss in calculated platelet function over time for heparinized whole blood. Curve 24 illustrates the loss in calculated platelet function over time for a sample of citrated whole blood obtained from the same individual. It can be seen that the loss in platelet function is significantly greater for the citrated blood sample than for the heparinized blood sample. However, some hospitals and laboratories would prefer to use citrated whole blood rather than heparinized blood for platelet function tests. Blood collection tubes containing a citrate collection medium (commonly referred to as "blue-top tubes") are commercially available, whereas collection tubes containing an appropriate quantity of heparin as the anticoagulant are not. Thus, the present invention offers a significant advantage over existing methods and apparatuses, by providing a solution to the instability problem associated with the use of citrated whole blood. More specifically, the present invention provides an improved test which reliably reflects the true in vivo platelet function, regardless of the amount of time the blood sample has been stored in citrate.

Figure 3:
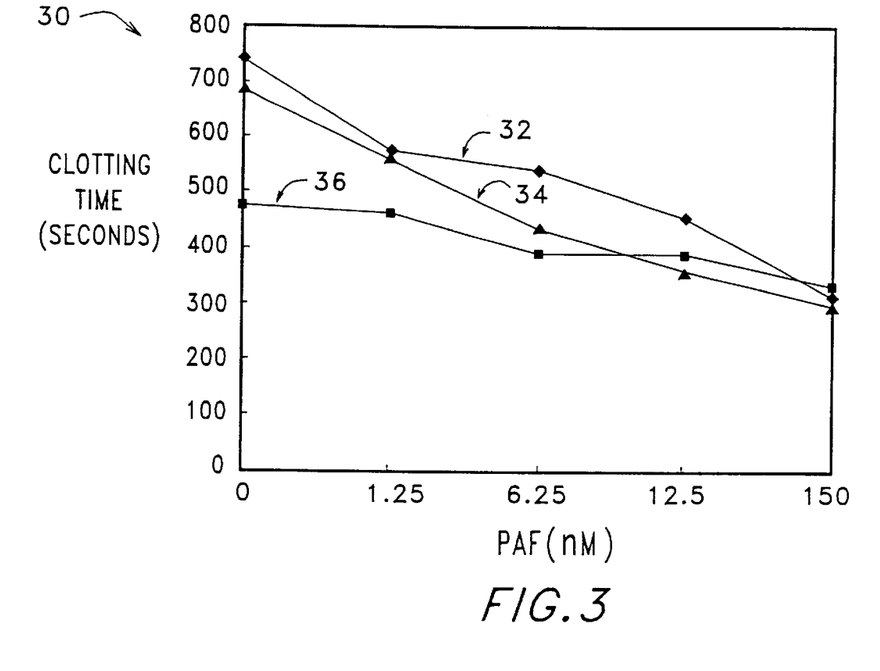
FIG. 3 is a graph similar to the graph of FIG. 1. The upper curve 32 of the graph represents the behavior of a sample of fresh whole blood, tested within one minute of drawing the sample. The middle curve 34 represents the behavior of the same blood collected in a 3.8% citrate collection medium (9:1 ratio) and stored for 45 minutes, then tested in a cartridge with 15 millimolar (mM) of additional calcium chloride. The bottom curve 36 represents the behavior of the same citrated blood (curve 34), but without adding calcium chloride prior to testing.

FIG. 3 presents curves 32, 34 and 36 which compare the baseline and activated clotting times of freshly drawn whole blood and samples of citrated whole blood, with and without a pre-test recalcification step. Curve 32 illustrates the baseline clotting time of fresh-drawn whole blood and the response of fresh blood to increasing PAF concentrations, similar to curve 12 in FIG. 1. Curve 34 illustrates the baseline and activated clotting times of a sample of citrated whole blood which has been incubated or mixed with a calcium source in a pre-test recalcification step prior to performing the platelet function test. Curve 36 illustrates the baseline and activated clotting times of a sample of citrated whole blood similar to curve 34, but without the pre-test recalcification step. Although the activated clotting times of curves 32, 34 and 36 are relatively similar, the baseline (non-activated) clotting times are significantly greater for both the fresh-drawn blood sample and the citrated blood sample which had been recalcified prior to testing. Consequently, because the baseline clotting time for the recalcified citrated blood sample is similar to that of fresh blood, the former sample provides an accurate representation of the in vivo coagulation conditions.

Figure 4:
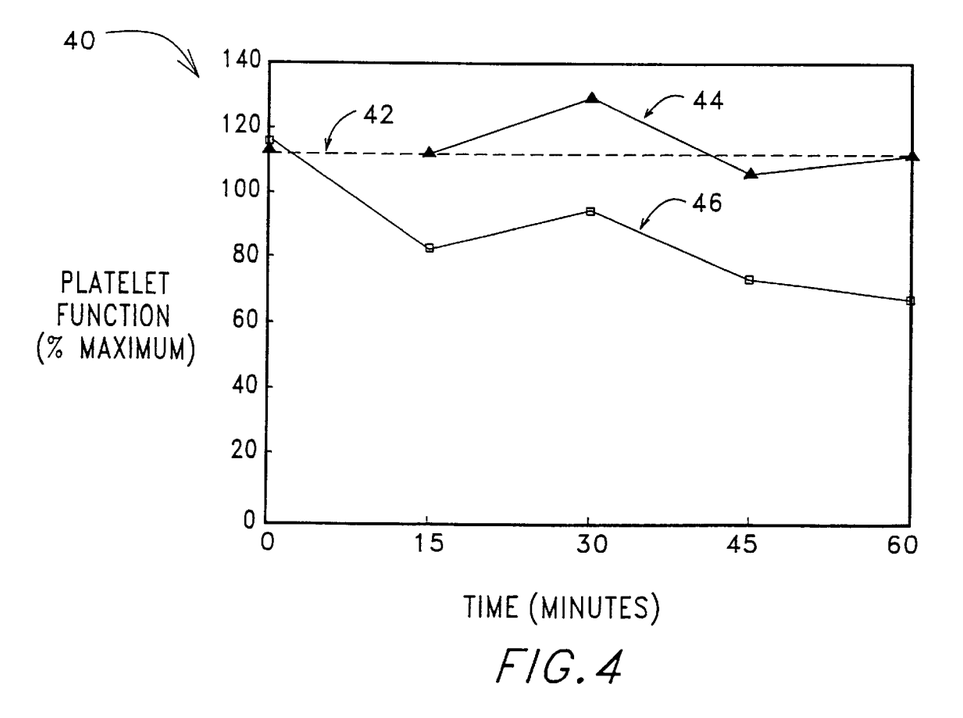
FIG. 4 is a graph similar to FIG. 2. The horizontal (broken) line 42 represents the baseline (non-activated) clotting time of a sample of fresh whole blood, tested immediately after drawing the sample. The upper curve 44 represents the behavior of the same blood collected in a 3.8% citrate collection medium (9:1 ratio) and stored for 45 minutes, then tested in a cartridge with 15 mM calcium chloride added prior to testing. The bottom curve 46 represents the behavior of the same citrated blood (curve 44), but without adding calcium chloride prior to testing.

FIG. 4 presents curves 44 and 46 which compare the changes in platelet function over time for two whole blood samples obtained from the same individual, one of which had been recalcified prior to testing (curve 44). Line 42 represents the baseline (non-activated) clotting time of the fresh-drawn whole blood, tested immediately after drawing the sample. Curve 44 illustrates the calculated platelet function over time for the citrated blood sample which had been incubated or mixed with a calcium source prior to commencing the test. Curve 46 illustrates the loss in platelet function over time for citrated whole blood which had not been recalcified prior to testing, similar to curve 24 in FIG. 2. It can be seen that the platelet function of the blood sample which had been recalcified prior to testing parallels the platelet function of the fresh-drawn sample (i.e., simulates the in vivo platelet function of the blood), even after 60 minutes of storage in citrate.

To practice the improved platelet function test of the present invention, which provides a reliable indication of the in vivo platelet function regardless of the amount of time which has elapsed since the sample was obtained, each of the test cells in the platelet function test cartridge includes a novel reagent composition. This novel reagent composition (shown in FIG. 7 as reagent composition 80 in reaction chamber 94) may be either a liquid or a solid powder, and includes three components: a platelet function restoration agent (hereinafter referred to as the "restoration agent"), an anticoagulant agent, and a predetermined amount of a platelet activating agent, as will be discussed below. The restoration agent may be any substance which reverses the loss in platelet function due to the presence of a calcium chelating agent, such as sodium citrate, i.e., any substance which restores the platelet function in the citrated blood sample to reflect the true in vivo (non-activated) platelet function. In the presently preferred embodiment of the invention, the restoration agent is calcium chloride. However, any substance which is known or found to be functionally equivalent to calcium chloride in restoring the platelet function of citrated blood may be used in the practice of the present invention. Thus, although calcium chloride is the presently preferred calcium salt for use in the invention, any calcium salt which functions in a similar manner to calcium chloride may be used in the invention. Similarly, although many blood coagulation reactions are currently believed to require calcium ions as cofactors, any substance which is known or subsequently found to be functionally equivalent to calcium in facilitating these coagulation reactions may be used, either individually or in combination with calcium, in the practice of the present invention.

The concentration of the restoration agent required to restore the platelet function of the blood sample to reflect the true in vivo (non-activated) platelet function will depend, in part, upon the concentration of the calcium chelating agent in the blood sample and the stoichiometry of the chelating and coagulation reactions. However, the concentration of the restoration agent must be sufficient to achieve optimal platelet function in the blood sample prior to performing the platelet function test, i.e., the concentration must be sufficient to realize maximum restoration effect such that any further increase in concentration has a negligible effect on baseline clotting time. With the presently preferred restoration agent, calcium chloride, the restoration agent concentration in the blood sample is between about 1 and about 50 millimolar, preferably between about 10 and about 20 millimolar, more preferably between about 12 and 18 millimolar, and most preferably between about 14 and 16 millimolar.

The anticoagulant agent of the reagent composition 80 prevents coagulation-related activities within the blood sample prior to commencement of the ACT test, i.e., the anticoagulant agent is added to the blood sample to prevent the initiation of coagulation-related reactions which might otherwise result from the presence of the restoration agent in the sample. For example, when calcium chloride (restoration agent) is introduced into a citrated blood sample, additional calcium ions become available which may participate in various coagulation-related activities, thereby negating the anticoagulant effects of citrate. Although additional citrate could be added to chelate the additional calcium and thus nullify the effects of the calcium chloride (thereby inhibiting pre-test coagulation), such an additive would be likely to adversely affect the ACT test results, by inhibiting the coagulation-related activities the ACT test is designed to detect. Thus, the anticoagulant agent of the reagent composition 80 must function in a manner other than by chelating calcium ions. In general, the anticoagulant agent may be any substance having anticoagulant activity and which is neither reactive with nor affected by the restoration agent or the other test components. A wide variety of suitable anticoagulant compounds are known and readily available to the art including, for example, heparin (an acid mucopolysaccharide) and argatroban ((2R,4R)-4-methyl-1-[$N_2$-(RS)-3-methyl-1,2,3,4-tetra-hydro-8-quinolinesulfonyl)-L-arginyl]-2-piperidinecarboxylic acid hydrate). In a particularly preferred embodiment, the anticoagulant agent is heparin, which, together with antithrombin III, accelerates the inhibition of activated factor X and thrombin.

The concentration of the anticoagulant agent in reagent composition 80 required to prevent the initiation of pre-test coagulation-related reactions will depend upon the anticoagulant activity of the particular agent. With the presently preferred anticoagulant agent, heparin, the anticoagulant agent concentration in the blood sample is between about 0.1 unit and about 10 units, preferably between about 1 unit and about 5 units, and more preferably between about 2 units and about 4 units per milliliter of blood sample.

The final component of the novel reagent composition 80 of the present invention is a platelet activating agent which serves as the chemical platelet activator to facilitate evaluation of the function of platelets in the blood sample to be tested. More specifically, the platelet activating agent enhances the ability of active platelets to effectively participate in the blood clotting reaction and thereby shortens the clotting time of the blood. If the platelets are inactive or not functioning normally, the platelet activating agent will have a lessened or no effect on the clotting time. Platelet activating agents are well known and readily available in the art. Suitable platelet activating agents for use in the methods and apparatus of the present invention include, without limitation, platelet activating factor (1-O-alkyl-2-acetyl-sn-glyceryl-3-phosphorylcholine, a biologically active phospholipid, commonly referred to as "PAF"), adenosine diphosphate (ADP), arachidonic acid, collagen, epinephrine, and ristocetin. In a particularly preferred embodiment, the platelet activating agent is PAF (described in Demopoulos, et al., *J. Biol. Chem.,* 254:9355–9358 (1979)).

Figure 7:
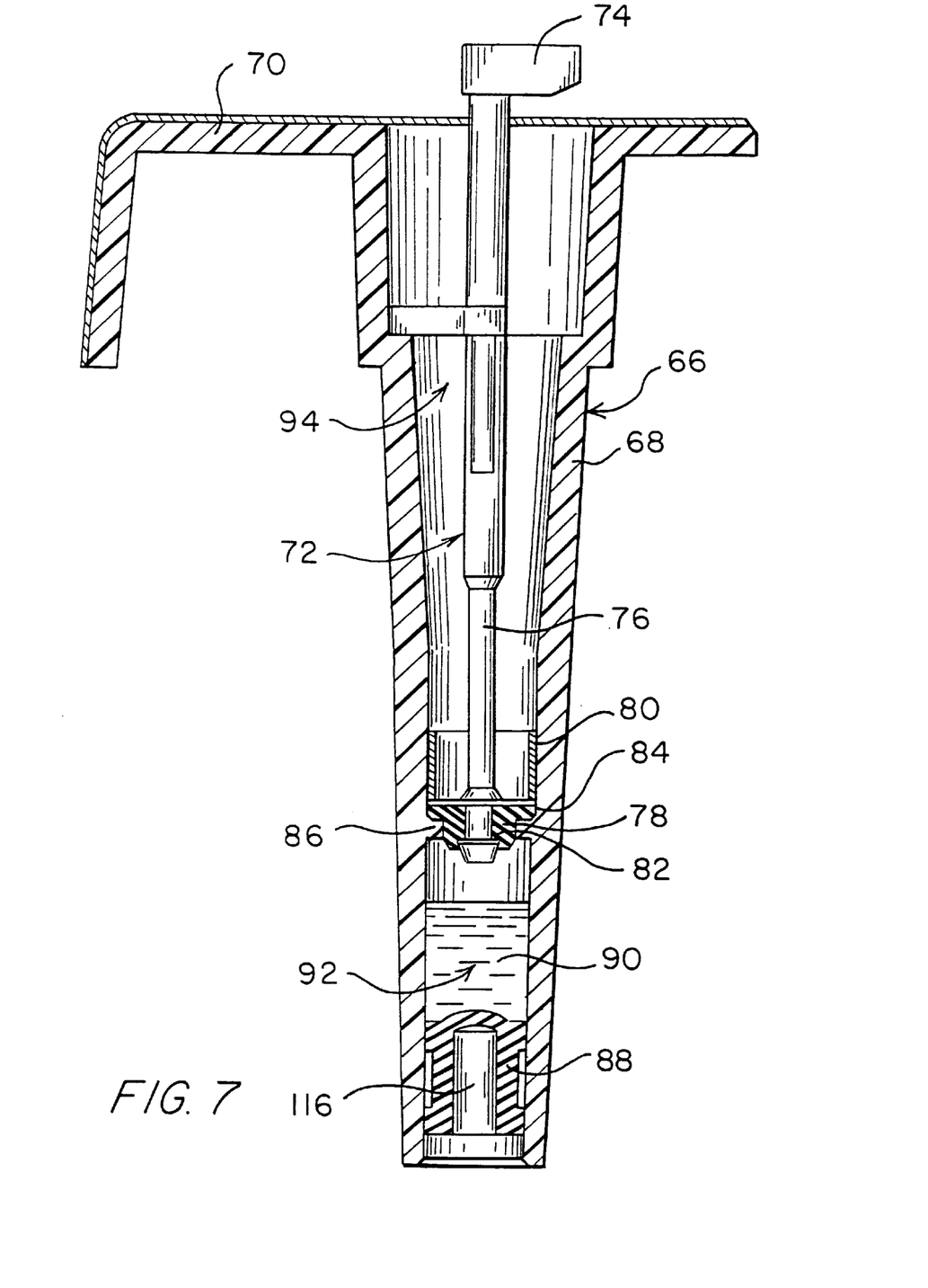
FIG. 7 is an enlarged vertical sectional view through one of the test cells of the plunger sensor cartridge, taken in the plane of line 7—7 shown in FIG. 6.

The specific concentrations of the platelet activating agent in reagent composition 80 of the present invention (i.e., reagent composition 80 in reaction chamber 94 of the test cell 66, shown in FIG. 7) will depend, in part, upon the activating efficiency of the particular agent. However, to determine the "baseline" or "non-activated" clotting time of the blood sample, the concentration of the platelet activating agent in at least one ("baseline") cell (e.g., cells 66A and 66B in cartridge 64) will be zero, regardless of the particular agent. With the exemplified platelet activating agent, PAF, the final concentration of platelet activating agent in the blood sample within the "activated" cell(s) of the test cartridge is between about 0.1 nM and about 10 $\mu$M, preferably between about 0.1 nM and about 3 $\mu$M, more preferably between about 0.1 nM and about 1 $\mu$M, and most preferably between about 1 nM and about 200 nM.

As discussed previously, reagent composition 80 of the present invention may be either a liquid or a solid powder, although a solid powder form (commonly referred to as a "dry fill") is preferred. To prepare reagent composition 80 as a solid or dry fill, predetermined amounts of the three components (restoration agent, anticoagulant agent, and platelet activating agent) are combined and mixed with a saline (NaCl) solution preferably containing a protein, such as bovine serum albumin, to stabilize the platelet activating agent. The mixture may be diluted, if necessary, with additional saline solution to achieve the desired platelet activating agent concentrations. A predetermined amount of each solution of reagent composition 80 is placed in the reaction chambers 94 of the test cells 66 (shown in FIGS. 5, 6 and 7) and allowed to evaporate, leaving a solid or dry fill residue of reagent composition 80.

In one embodiment of the invention, at least two of the test cells comprise different amounts of the platelet activating agent, thus providing a series of differing clotting times. In the exemplified embodiment shown in FIG. 6, for example, the first two cells 66A and 66B contain no platelet activating agent (the "baseline " cells). However, each successive cell 66C, 66D, 66E, and 66F includes increasing amounts of platelet activating agent. Although the concentrations and proportions may vary depending upon the particular reagent components (as discussed above), the following table provides an illustration of suitable concentrations of the presently preferred components in reagent composition 80, following dilution with the blood sample:

TABLE 1

Concentrations of Components in Reagent Composition 80
(Test Cartridge 64)

| Reagent | Cell 66A | Cell 66B | Cell 66C | Cell 66D | Cell 66E | Cell 66F |
| --- | --- | --- | --- | --- | --- | --- |
| PAF | 0.0 ng | 0.0 ng | 1.25 nM | 6.25 nM | 12.5 nM | 150 nM |
| Heparin | 3 units/ml | 3 U/ml | 3 U/ml | 3 U/ml | 3 U/ml | 3 U/ml |
| Calcium chloride | 15 mM | 15 mM | 15 mM | 15 mM | 15 mM | 15 mM |

The improved ACT test of the present invention also includes a clotting reagent in the reagent chamber (shown in FIG. 7 as reagent chamber 92) of each test cell 66. The clotting reagent (discussed below and shown in FIG. 7 as clotting reagent 90) includes a platelet activator (commonly referred to as a surface activator), such as kaolin, to activate blood Factors XII and/or XI. However, as will be appreciated by those of skill in the art, other platelet activating reagents which function in a similar manner to kaolin may be used for the practice of the invention, such as diatomaceous earth. The clotting reagent 90 may be present in either a solid or liquid form, although the presently preferred reagent is in a liquid form. To prepare a liquid clotting reagent 90, the activator component may be dissolved in an appropriate buffered solution, a variety of which are known to those skilled in the art, including HEPES (hydroxyethylpiperazine ethanesulfonic acid) buffer. A bacteriostatic agent such as sodium azide may also be included in clotting reagent 90. In a particularly preferred embodiment, clotting reagent 90 comprises kaolin, HEPES buffer, calcium chloride (to achieve a linear clotting time response), and sodium azide as the bacteriostatic agent. As discussed more fully below, and as illustrated in the examples hereof, an appropriate amount of clotting reagent 90 is introduced into the reagent chamber 92 of each cell of the test cartridge 64, 65.

To determine the platelet function in accordance with one embodiment method of the present invention, a predetermined volume of blood to be analyzed is introduced into the reaction chamber 94 of each test cell 66A–66F, thereby dissolving reagent composition 80. The resulting blood mixture is then allowed to react at a sufficient temperature and for a sufficient period of time to facilitate interaction between the platelets and restoration agent, thereby maximizing the restoration of platelet function. Preferably, the blood sample and reagent composition 80 are incubated at a temperature of between about 36° C. and about 38° C. and for a period of between about 1 second and about 2 minutes. During this incubation period, referred to herein as the pre-test recalcification step, the platelet function in the citrated blood sample is increased to a level which is generally comparable to the in vivo platelet function. Contemporaneously with the pre-test recalcification, the anticoagulant agent in the reagent composition 80 combines with certain components within the blood sample to inhibit pre-test coagulation and coagulation-related reactions. Although in the presently preferred embodiment the restoration and anticoagulant agents are included as test reagents within the test cell 66, it is anticipated that these novel reagents could be combined with the blood sample outside the test cell 66. The resulting blood mixture may then be allowed to react outside the test cell 66 or, alternatively, transferred to the test cell for recalcification prior to the initiation of the ACT test. The present invention thus includes these various modifications and alternate embodiments.

Following the pre-test recalcification step, the clotting reagent 90 in each reagent chamber 92 is introduced into the corresponding reaction chamber of each test cell 66A–66F, and the clotting time is determined. The clot ratio is then calculated based on the clotting time for each test cell. Specifically, the clot ratio is defined as one minus the ratio of the average activated clotting time (i.e., the average clotting time of cells comprising the same concentration of platelet activating agent) to the average control clotting time (e.g., cells 66A and 66B). Platelet function (shown in FIGS. 2 and 4) is expressed as a percentage of the maximum clot ratio response observed in a normal population. This value of a normal population response is known and can be used to compute the clot ratio percentage, which is in turn indicative of the platelet functionality. As will be understood by those of skill in the art, any appropriate desired calculation may be made from the relative clotting times in each cell. The platelet functionality can in turn be utilized to estimate the risk of blood loss during or after surgery and the need for a transfusion of blood components. The platelet functionality may further assist in managing heparin therapy during invasive cardiology procedures.

Although the present invention is exemplified using coagulation-related platelet assays, including those described in U.S. Pat. Nos. 5,314,826 and 5,925,319, the invention can be applied to other, non-exemplified platelet function assays carried out on citrated blood. Such platelet function assays include, for example, platelet function tests to measure the platelet release reaction and platelet aggregation, and assay for von Willebrand's Factor. The present invention may also be readily modified to accommodate a variety of specialized coagulation tests, including specific coagulation factor assays, tests for disseminated intravascular coagulation, and the heparin-independent, high sensitivity platelet function evaluation technique described in U.S. Pat. No. 6,010,911, issued on Jan. 4, 2000 which is assigned to the assignee of the present invention and incorporated herein by reference. As will be understood by those of skill in the art, the present invention can be practiced with any platelet function assay, including the above-referenced techniques, by including a pre-test recalcification step, i.e., by incubating the restoration agent and anticoagulant agent in the citrated blood sample prior to commencing the test.

Figure 5:
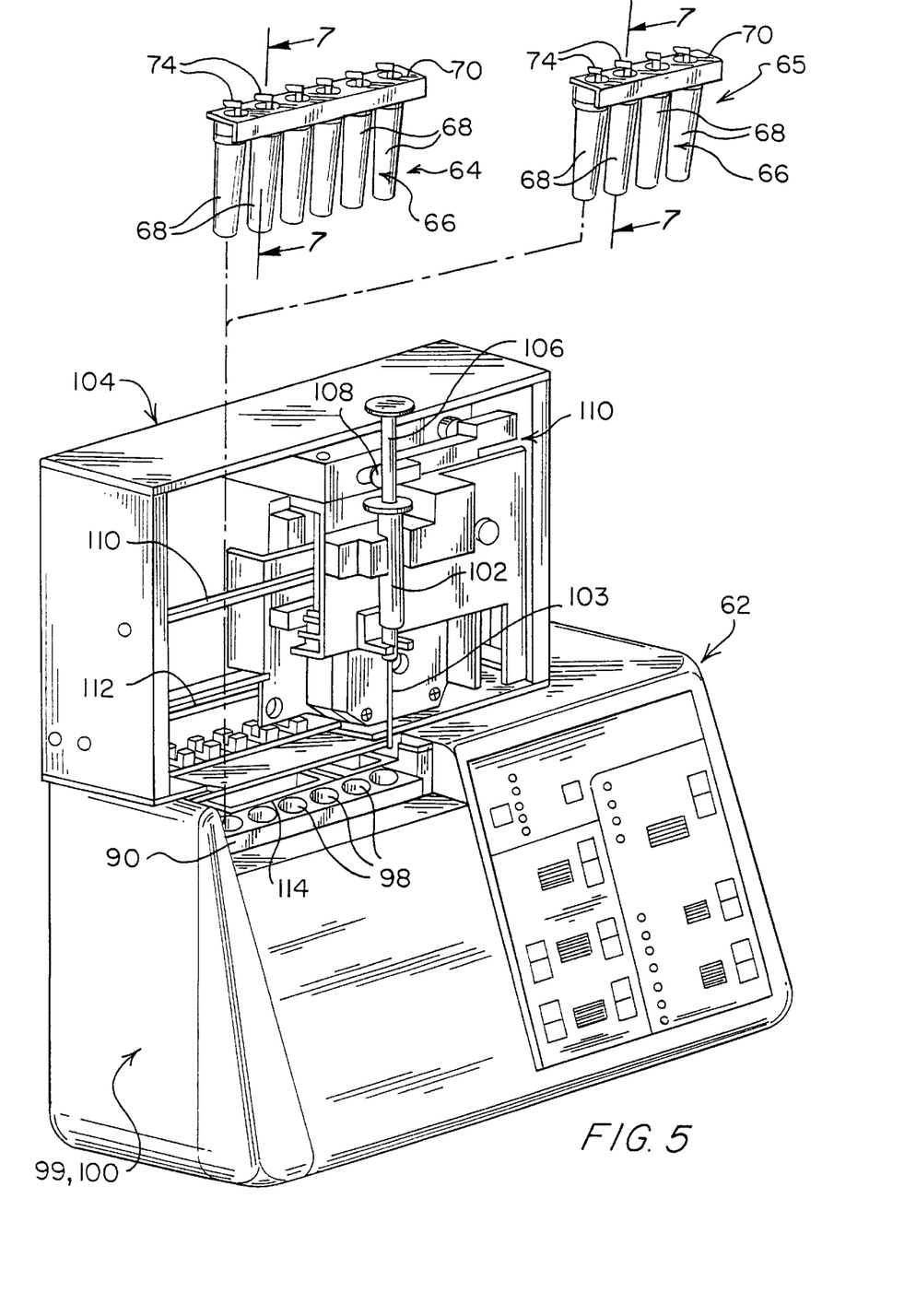
FIG. 5 is a perspective view of a 6-channel plunger sensor cartridge, a 4-channel plunger sensor cartridge, and a high sensitivity coagulation detection apparatus with which the cartridges are used on selectively alternate basis, all of which comprises an apparatus for measuring and detecting coagulation and coagulation-related factors in fluids, in accordance with the present invention.
Figure 6:
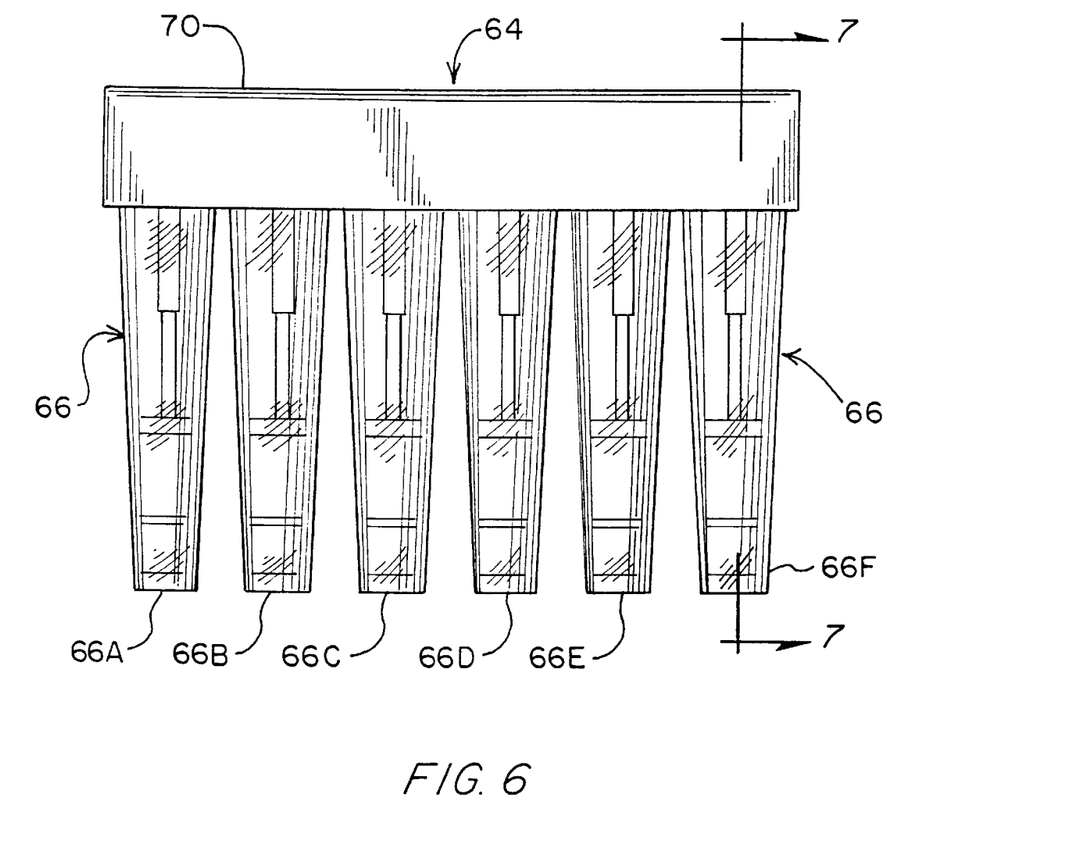
FIG. 6 is a front elevational view of the 6-channel plunger sensor cartridge shown in FIG. 5.

Referring now to FIGS. 5, 6 and 7, the presently preferred embodiment of an apparatus 62 and a plunger sensor cartridge 64 may be used together in order to perform a platelet function test using two unique reagents, i.e. a substance to restore the platelets to their normal in vivo condition and an anticoagulant to inhibit pre-test coagulation-related activities. Although the invention is exemplified using a 6-cell cartridge (cartridge 64 in FIGS. 5 and 6), the invention can be practiced using any multiple-cell cartridge, for example, using the alternate 4-cell cartridge (cartridge 65) shown in FIG. 5. In general, the ACT test of the invention can be achieved by comparing the clotting times of two test cells, one without a platelet activating agent and the other with an appropriate (generally high) amount of platelet activating agent. Preferably, the ACT test is performed in duplicate or triplicate, with the platelet function calculations being based on the average clotting time for each concentration of platelet activating agent.

In general, the ACT test, platelet function test, and heparin-protamine titration tests which may be performed using the apparatus 62 and the cartridges 64, 65 have previously been described in the assignee's aforementioned patents and applications, including U.S. Pat. Nos. 4,599,219 and 5,925,319, the disclosures of which are incorporated herein by reference. Accordingly, many of the details of functionality will be generalized herein with the understanding that the assignee's prior patents and applications disclose many of these details to a greater extent. It is anticipated that coagulation-related testing techniques other than the plunger techniques may also be used to perform an ACT test using these novel reagents, in accordance with this invention. It is anticipated that similar results and effects as those obtained from using the assignee's plunger sensor technique will also be obtainable by practicing the present invention using other well known methods and devices.

In general, the cartridges 64, 65 as shown in FIGS. 5 and 6 include a plurality of test cells 66 (shown in FIG. 7), each of which is formed generally as a downward extending truncated tube-like member 68. Each of the tube-like members 68 is connected to an upper shelf portion 70. A plunger assembly 72 (also shown in FIG. 7) extends downward from an upper open end of each test cell 66 into the tube-like member 68. Each plunger assembly 72 includes at least one and preferably a pair of flags 74 at the upper end located at a position above the shelf portion 70. The plunger assembly 72 also includes a shaft 76 which extends from the flags 74 downward to a lower end upon which a disk member 78 is attached. The disk member 78 is formed of resilient material and includes a center, generally cylindrical main body portion 82 and an annular flange 84 located above and extending outward from the main body portion 82. The annular flange 84 includes slots or openings (not shown) formed therein at outer circumferential locations.

As shown in FIG. 7, prior to using the plunger sensor cartridge 64 or 65 in the apparatus 62, the disk member 78 is positioned with its main body portion 82 located in and sealed against an opening formed by a partition 86 extending inwardly from the tube-like member 68. The partition 86 is located between the upper and lower open ends of the tube-like member 68. A resilient flexible plug 88 is positioned in the interior of the tube-like member at its lower open end. The plug 88 seals against the inner side walls of the tube-like member 68 and confines a quantity of clotting reagent 90 (discussed above) in a reagent chamber 92 between the partition 86 and the plug 88. The clotting reagent 90 may be a liquid or a solid powder. A reaction chamber 94 is generally defined by that portion of the open tube-like member 68 above the partition 86. A predetermined amount of a reagent composition 80, the contents of which have been described in detail above, is provided in the reaction chamber 94 as either a liquid or a solid powder.

The plunger sensor cartridge 64 or 65 is inserted into a receiving block (not shown) in the apparatus 62 to conduct the test. Each of the test cells 66 extends into a receptacle 98 of the receiving block. Each receptacle 98 has a configuration adapted to receive a test cell 66, while the shelf portion 70 of the cartridge 64 or 65 sits on top of the receiving block.

The apparatus 62 is generally formed of subassemblies. A dispensing subassembly 104 of the apparatus 62 automatically supplies a sample of blood to each test cell 66 of the cartridge 64 or 65. The reagent composition 80 is dissolved in the blood sample when the blood sample is introduced into the reaction chamber 94. A plunger lifting assembly 99 of the apparatus 62 controls the lifting movement of the plunger assembly 72, and a reagent drive subassembly 100 of the apparatus 62 moves the plug 88 to force the clotting reagent 90 into the reaction chamber 94, thereby mixing the clotting reagent 90 with the reagent composition 80. An optical sensing system (not shown) senses the physical descent of the plunger assembly 72 through the blood sample and reagent mixture in the reaction chamber 94 in order to detect coagulation condition.

The sample of blood is supplied to the reaction chamber 94 from a syringe 102 having a blunt needle 103 attached thereto. The syringe 102 is manually attached to the dispensing subassembly 104 of the apparatus 62. The body of the syringe 102 contains blood, preferably fresh drawn from the patient, upon which the ACT test is to be performed. Of course, prior to attachment of the syringe 102 to the dispensing subassembly 104, all air or other voids in the blood within the syringe 102 and the blunt needle 103 is removed in the conventional manner. A plunger 106 located within the body of the syringe 102 is engaged with a drive wheel 108. Rotation of the drive wheel 108 forces the syringe plunger 106 downward and expels a predetermined amount of blood from the lower end of the blunt needle 103. The extent to which the syringe plunger 106 is moved downward determines the quantity of blood expelled from the needle.

The dispensing subassembly 104 includes a movement frame 110 which is moved laterally in the horizontal direction along guide rods 112. The degree of lateral movement is controlled by the microprocessor (not shown) of the apparatus 62 in accordance with programmed information, thereby locating the blunt needle 103 directly above the open upward ends of each test cell 66 of the cartridge 64 or 65. After attaining the proper lateral location, the movement frame 110 moves the syringe 102 vertically downward to insert the lower end of the blunt needle 103 into each of the test cells 66. The desired amount of blood sample is automatically dispensed into the test cell 66. Thereafter, the blunt needle 103 is withdrawn from the test cell 66 by the movement frame 110, and the next lateral position over a test cell 66 is assumed. The sequence again repeats itself, thereby injecting into each test cell 66 of the plunger sensor cartridge 64 or 65 that predetermined amount of blood sample needed for conducting the ACT test.

A portion of the plunger lifting subassembly 99 is shown in FIG. 5, and includes at least one and preferably a plurality of lift wires 114. The lift wires 114 are positioned in a lowermost location, and in that position a horizontal segment of the lift wires 114 fits underneath the flags 74 of the plunger assembly 72. Upward movement of the lift wires 114 lifts each of the plunger assemblies 72 upward, thereby removing the disk member 78 from its sealed location in the opening 84 of the partition 86. A fluid communication passageway through the opening 84 between the reagent chamber 92 and the reaction chamber 94 is thereby established. The reagent drive subassembly 100 includes a plurality of plug driver shafts 116 (shown in FIG. 7). Thereafter, or simultaneously with the upward movement of the plunger assembly 72, the plug driver shafts 116 of the reagent drive subassembly 100 move upward, forcing each plug 88 upward collapsing the reagent chamber 92 and forcing its contents 90 into the reaction chamber 94.

At the commencement of the ACT test, a sample of blood upon which the test is to be performed is introduced into the reaction chamber 94. The reagent composition 80 is then dissolved in the sample of blood and allowed to mix therewith for a sufficient period of time to effect recalcification of the blood sample. Following completion of the recalcification step, the lift wires 114 of the subassembly 99 lift the plunger assembly 72 to withdraw the disk member 78 from its seated engagement with the opening in the partition 86. The plug 88 is pushed upward against the partition 86 by the plug driver shafts 116 of the subassembly 100. The clotting reagent 90 from the reagent chamber 92 is forced through the opening into the reaction chamber 94. The clotting reagent 90 is mixed with the blood and reagent mixture in the reaction chamber 94, by reciprocating the plunger assembly 72. The lift wires 114 of the subassembly 99 continue to lift the plunger assembly 72, which descends by the force of gravity through the pool of fluid in the reaction chamber 94. Throughout the test, the activation of platelets by shear stress in the blood sample is kept to a minimum, as described in U.S. Pat. No. 5,314,826. As the plunger assembly 72 descends through the fluid it is resisted by a property of the fluid in the reaction chamber 94, such as the viscosity, which changes as a result of the onset or occurrence of a coagulation-related activity, e.g., platelet activation and aggregation followed by coagulation resulting in fibrin formation. The descent rate of the plunger assembly 72 therethrough is changed, which indicates the occurrence of a coagulation-related activity. The clotting time of a blood sample is determined as described in detail in the assignee's aforementioned patents and applications, including U.S. Pat. Nos. 4,599,219 and 5,925,319.

It will be appreciated that clinical trials may establish a quantitative correlation between platelet functionality and any medical treatment to be administered. For example, during heart bypass surgery the platelets of blood circulated in an extracorporeal circuit may become activated by the materials present in the extracorporeal circuit. This activation may be reversible or irreversible. Once platelets are irreversibly activated they lose their ability to function further. A deficiency of functional platelets in the blood may be indicative of an increased probability of a post-operative bleeding problem. Such a deficiency, and the, resulting post-operative bleeding risk, could be remedied by a transfusion of platelet concentrate. The platelet functionality test can identify a deficiency of platelets or functional platelets and aid the attending physician in ascertaining when to administer a platelet concentrate transfusion. Such a test is further useful in ascertaining the efficacy of a platelet transfusion. By performing the platelet functionality test following a platelet transfusion it is possible to determine if additional platelet concentrate transfusions are indicated. Because the present invention is not dependent upon the amount of the time which has elapsed since the sample was drawn, it is especially useful for situations which require that the sample be transported from the patient to a different location for evaluation, i.e., where an automated coagulation detection apparatus is not readily available. For example, it is often desirable to perform a platelet function test after a patient has been moved from the operating room to the intensive care unit. In such a case, the blood sample must be transported back to the operating room or to another location such as a clinical laboratory for testing. The present invention thus provides a convenient alternative to bedside testing, by allowing hospital personnel to transport blood samples for testing without concern for distance from the laboratory and without the need for recording time of draw and instructions regarding the timing of the test.

The invention is further described by the following examples which are illustrative of specific modes of practicing the invention and are not intended as limiting the scope of the invention as defined by the appended claims.

EXAMPLES

All solvents and reagents employed in the examples were used as received from the manufacturer. Bovine serum albumin (BSA) was purchased from Sigma Chemical Co. (St. Louis, Mo.; Sigma Product #A-3803); bovine lung heparin was purchased from The Upjohn Company (Kalamazoo, Mich.); PAF was purchased from Sigma Chemical Co. (St. Louis, Mo.; Sigma Product #P-9525); calcium chloride dihydrate was purchased from Fisher Scientific (A.C.S. certified; Prod. No. C79-500); and kaolin was obtained from Charles Crystal, Inc. (St. Austell, Cornwall, UK). The coagulation detection apparatus used to perform the ACT tests in the examples was manufactured by Medtronic Hemotec, Inc. (Englewood, Colo.; Prod. No. 305-02).

Example 1

Preparation of Test Cells Comprising Reagent Composition 80 and Clotting Reagent 90

This example demonstrates the preparation of test cells to perform an ACT test on a sample of citrated whole blood which is independent of the amount of time which has elapsed since the sample was drawn, in accordance with the present invention. The procedure for preparing the test cells comprises the following steps:

1. Clotting Reagent: Weigh out 4 g Kaolin. Add 5 ml of 1.0 M calcium chloride solution. Dilute mixture to 100 ml with hydroxyethyl-piperazine ethanesulfonic acid (HEPES) buffer. This provides 4% w/v suspension of kaolin in HEPES buffer, 0.05 M calcium, pH 7.3. Add 0.088 ml of this kaolin mixture into the reagent chamber 92 of each cell 66 in the test cartridge.

2. Reagent Stock Solutions:
   1) BSA/NaCl diluent. Combine 250 mg BSA and 876 mg NaCl, and bring to 100 ml with deionized water. This solution is 0.25% BSA (wt/vol) and 0.15 M NaCl.
   2) Heparin reagent stock. Prepare 1050 units/ml heparin stock solution by bringing 1.05 ml of 10,000 units/ml heparin to a final volume of 10 ml with HEPES buffer.
   3) Calcium stock. Prepare 1 M calcium stock by dissolving 3.675 grams of calcium chloride dihydrate in 25 ml BSA/NaCl diluent.
   4) PAF stock. Using a Hamilton syringe, pipette 50 µl platelet activating factor (PAF) into a clean vial and allow the chloroform solvent to evaporate. Add 2 ml BSA/NaCl diluent and stir continuously for at least 1 hour. This provides a 100 µM working stock of PAF.

3. Baseline Reagent. Combine 0.5 ml heparin reagent stock, 2.625 ml 1M calcium stock, and 6.875 ml BSA/NaCl diluent to provide 10 ml baseline reagent (3 units/ml heparin; 15 mM calcium).

4. Platelet Activation Reagent. Combine 0.5 ml heparin reagent stock, 2.625 ml 1M calcium stock, 6.7875 ml BSA/NaCl diluent, and 0.0875 ml PAF stock to provide 10 ml platelet activation reagent (3 units/ml heparin; 15 mM calcium; and 50 nM PAF).

5. Cartridge preparation.
   1) Baseline clotting time cell(s). To determine the baseline (non-activated) clotting time, add 0.02 ml of baseline reagent to each of the "baseline clotting time" cells (e.g., cells 66A–B or cells 66A–C of cartridge 64).
   2) "Activated" clotting time cell(s). To determine the activated clotting time, add 0.02 ml of platelet activation reagent to each of the "activated clotting time" cells (e.g., cells 66C–F or cells 66D–F of cartridge 64).
6. The water is allowed to evaporate, leaving a dry fill in each cell.
7. Using a sample of normal blood from a voluntary donor, and a cartridge prepared as described above, 0.35 ml aliquots of blood are added to each cell and the clotting time of the blood in each cell is determined and plotted as previously described.

The titration curve can be normalized by converting the clotting times to ratios. The average clotting time of Cell A and Cell B, with no platelet activating factor present, is the cell clotting time to which all other cell clotting times are compared. The ratio is calculated by dividing the average of Cell A and Cell B clotting time in seconds by each other cell clotting time in seconds. A clot ratio is then calculated as 1 minus the ratio of the average of Cell A and Cell B clotting time to other cell clotting times (1—average of CellA&Btime/CellXtime). Data can also be presented in terms of platelet function as a percentage of normal. This is calculated from the clot ratio by multiplying the clot ratio by 100 and then by a factor which is determined by measuring the maximum platelet activating factor response from at least 20 normal donors. These donors had no known platelet dysfunction and were taking no known medications.

The test cartridge and method described herein are useful for providing a simple and rapid platelet function assay. This assay can identify patients with low platelet function. This is useful for those patients with excessive post-cardiopulmonary bypass blood loss (due to a platelet-related disorder) so that appropriate platelet transfusion can be administered. In addition, those patients experiencing excessive post-cardiopulmonary bypass blood loss who are found to have normal platelet function can be treated appropriately, thus avoiding the need for expensive platelet therapy and the health risks associated with blood component transfusion.

Example 2
Preparation of Test Cells for Comparing Activated Clotting Times and Calculated Platelet Function of Whole Blood Samples This example demonstrates the preparation of test cells to perform platelet function and ACT tests on samples of freshly drawn whole blood, citrated whole blood, and heparinized whole blood. The test cells were prepared essentially as described above in Example 1, except for the following modifications:

Cartridge Preparation
1) Baseline clotting time cell(s). Prepared as described in Example 1, paragraph 2(1). Add 0.02 ml to each of cells 66A and 66B.
2) "Activated" clotting time cell(s). To prepare cells with varying concentrations of platelet activating agent, dilute a volume of PAF stock (prepared as described in Example 1) using BSA/NaCl diluent (also prepared as described in Example 1) to the indicated final volume, as follows:

| Cell | Volume of PAF Stock | Final Volume |
|------|---------------------|--------------|
| 66C  | 0.01095 ml          | 50 ml        |
| 66D  | 0.02735 ml          | 25 ml        |
| 66E  | 0.0547 ml           | 25 ml        |
| 66F  | 0.65625 ml          | 25 ml        |

Add 0.02 ml of each of the above PAF solutions to the appropriate cell (cells 66C–66F).

A. Heparinized Blood Samples
Heparinized blood samples were tested in cartridge 64 using the PAF solutions (cells 66C–66F) as described above.

B. Citrated Blood Samples without Additional Calcium
Citrated blood samples were tested in cartridge 64 comprising the PAF solutions (cells 66C–66F), as described above, and 3 units/ml heparin. Test cells were prepared essentially as described above, except that 0.01 ml of a heparin solution (described below) was added to each cell and allowed to dry. The heparin solution was prepared by bringing 1.05 ml heparin (10,000 units/ml) to a final volume of 100 ml with HEPES buffer.

C. Citrated Blood Samples with Additional Calcium
Test cells were prepared essentially as described above for the citrated samples without additional calcium, except that additional calcium chloride was added prior to testing as follows. Prepare 1 M calcium stock in HEPES buffer by dissolving 14.7 grams of calcium chloride dihydrate in 100 ml HEPES buffer. Prepare a diluted calcium stock by bringing 13.125 ml of 1 M calcium stock to a final volume of 25 ml with HEPES buffer. Add 0.01 ml of the diluted calcium stock to each cell (i.e., final calcium concentration is 15 mM per cell). Allow to dry. 0.35 ml aliquots of blood were added to each cell and the clotting time of the blood was determined and plotted as described above.

The results of platelet function tests on whole blood are shown in FIGS. 1 and 3. Data can also be presented in terms of platelet function as a percentage of normal, as shown in FIGS. 2 and 4.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

We claim:
1. A method for performing an activated clotting time test on a sample of citrated blood containing platelets, said method comprising the steps of:
   combining a platelet function restoration agent, an anticoagulant agent, a platelet activating agent, and the sample of citrated blood to be tested to form a test mixture, wherein said anticoagulant agent excludes any agent which serves to chelate calcium ions;
   activating the platelets of the sample by adding a clotting reagent to the test mixture at the start of the activated clotting time test;
   terminating the activated clotting time test upon detecting a predetermined change in a property of the test mixture; and
   calculating the activated clotting time of the sample of citrated blood based on the elapsed time from the addition of the clotting reagent to the test mixture to the point in time at which said predetermined change in the property of the test mixture occurs.

2. A method as defined in claim 1, wherein the platelet function restoration agent is calcium chloride.

3. A method as defined in claim 1, wherein the platelet function restoration agent is present at a concentration of between about 10 and about 20 millimolar.

4. A method as defined in claim 1, wherein the anticoagulant agent is heparin.

5. A method as defined in claim 1, wherein the anticoagulant agent is present at a concentration of between about 1 unit and about 5 units per milliliter of blood sample.

6. A method as defined in claim 1, wherein the clotting reagent is kaolin or diatomaceous earth.

7. A method as defined in claim 1, wherein the clotting reagent is kaolin.

8. A method as defined in claim 1, wherein the platelet activating agent is selected from the group consisting of 1-0-alkyl-2-acetyl-sn-glyceryl-3-phosphorylcholine, adenosine diphosphate, arachidonic acid, collagen, epinephrine, and ristocetin.

9. A method as defined in claim 1, wherein the platelet activating agent is 1-0-alkyl-2-acetyl-sn-glyceryl-3-phosphorylcholine.

10. A method as defined in claim 1, wherein the platelet activating agent is present at a concentration of between about 0.1 nM and about 3 $\mu$M.

11. A method as defined in claim 1, wherein the activated clotting time test is performed using a plunger sensor technique.

12. A method for performing an activated clotting time test on a sample of citrated blood containing platelets using a plunger sensor apparatus, said apparatus comprising at least one test cell and a plunger assembly within said test cell, wherein said test cell includes a reaction chamber and a reagent chamber, wherein said reaction chamber comprises a platelet function restoration agent, an anticoagulant agent, wherein said anticoagulant agent excludes any agent which serves to chelate calcium ions, and a platelet activating agent, and wherein said reagent chamber comprises a clotting reagent, said method comprising the steps of:

dispensing a sample of citrated blood containing platelets into the reaction chamber to form a first test mixture;

combining said first test mixture with the clotting reagent from the reagent chamber to form a second test mixture;

reciprocating the plunger assembly in the second test mixture by alternately lifting the plunger assembly and allowing the plunger assembly to descend through the test mixture;

detecting a point in time at which a predetermined property of the second test mixture changes by a predetermined expected amount by sensing the descent of the plunger assembly, the predetermined property affecting the activated clotting time test;

measuring an elapsed time from the beginning of the step of combining the first test mixture with the clotting reagent to the point in time at which the predetermined property of the second test mixture changes by the predetermined expected amount; and calculating the activated clotting time of the sample of citrated blood based on the elapsed time.

13. A method as defined in claim 12, wherein said step of dispensing a sample of citrated blood into the reaction chamber and said step of combining said first test mixture with the clotting reagent are separated by a period of between about 1 second and about 120 seconds.

14. A method for performing an activated clotting time test on a sample of citrated blood containing platelets using a plunger sensor apparatus, said apparatus comprising at least one test cell and a plunger assembly within said test cell, wherein said test cell includes a reaction chamber and a reagent chamber, wherein said reaction chamber comprises a sufficient quantity of calcium chloride to achieve optimal platelet function in the citrated blood sample, heparin, and platelet activating factor, and wherein said reagent chamber comprises kaolin, said method comprising the steps of:

dispensing a sample of citrated blood into the reaction chamber to form a first test mixture;

combining said first test mixture with the kaolin from the reagent chamber to form a second test mixture;

reciprocating the plunger assembly in the second test mixture by alternately lifting the plunger assembly and allowing the plunger assembly to descend through the test mixture;

detecting a point in time at which a predetermined property of the second test mixture changes by a predetermined expected amount by sensing the descent of the plunger assembly, the predetermined property affecting the activated clotting time test;

measuring an elapsed time from the beginning of the step of combining the first test mixture with the kaolin to the point in time at which the predetermined property of the second test mixture changes by the predetermined expected amount; and calculating the activated clotting time of the sample of citrated blood based on the elapsed time.

* * * * *